United States Patent
Hayashi et al.

(10) Patent No.: US 7,585,814 B2
(45) Date of Patent: Sep. 8, 2009

(54) METHOD OF CULTIVATING POTATO IN AN INCREASED YIELD

(75) Inventors: Toshio Hayashi, Wakayama (JP); Masatoshi Kamei, Wakayama (JP); Takayuki Nomura, Wakayama (JP)

(73) Assignee: Kao Corporation, Tokyo (JP)

( * ) Notice: Subject to any disclaimer, the term of this patent is extended or adjusted under 35 U.S.C. 154(b) by 367 days.

(21) Appl. No.: 11/189,831

(22) Filed: Jul. 27, 2005

(65) Prior Publication Data

US 2006/0030490 A1 Feb. 9, 2006

(30) Foreign Application Priority Data

Aug. 6, 2004 (JP) ............................. 2004-230314

(51) Int. Cl.
*A01N 25/00* (2006.01)
*A01N 25/02* (2006.01)
*A01N 25/04* (2006.01)

(52) U.S. Cl. .................................. 504/116.1; 504/357

(58) Field of Classification Search .............. 504/116.1, 504/353

See application file for complete search history.

(56) References Cited

U.S. PATENT DOCUMENTS

| 2,576,081 | A | * | 11/1951 | Tischler et al. ........... 504/116.1 |
| 4,167,641 | A | | 9/1979 | Welebir |
| 6,489,269 | B1 | * | 12/2002 | Hayashi et al. ............. 504/353 |
| 6,884,759 | B2 | * | 4/2005 | Hayashi et al. ............. 504/353 |
| 2004/0141822 | A1 | * | 7/2004 | Hiller ..................... 408/115 R |
| 2004/0142822 | A1 | * | 7/2004 | Suzuki et al. ............... 504/351 |

FOREIGN PATENT DOCUMENTS

| JP | 55-40674 | 3/1980 |
| JP | 9-322647 | 12/1997 |
| JP | 2000-198703 | 7/2000 |
| JP | 2002-265305 | 9/2002 |

OTHER PUBLICATIONS

Kumar et al, New Phytol. (1972), 71, pp. 639-648.

* cited by examiner

*Primary Examiner*—Johann R Richter
*Assistant Examiner*—Courtney Brown
(74) *Attorney, Agent, or Firm*—Oblon, Spivak, McClelland, Maier & Neustadt, P.C.

(57) ABSTRACT

The invention provides a method of cultivating potato. In the invention, Compound (A) of a specified structure having a C10 to C22 hydrocarbon group is applied at least once in a period from a planting stage to a flowering stage of potato.

6 Claims, No Drawings

METHOD OF CULTIVATING POTATO IN AN INCREASED YIELD

FIELD OF THE INVENTION

The present invention relates to a method of cultivating potato such as white potato(*Solanum tuberosum* L.) and sweet potato(*Ipomoea batatas* Lam.) in an increased yield.

BACKGROUND OF THE INVENTION

An attempt to increase the yield by promoting the growth of crops and increasing the yield per unit area is a task important in agricultural production. Usually, major three elements essential for plant growth, that is, nitrogen, phosphorus and potassium, and nutrient elements such as trace metal elements, are incorporated into a basal fertilizer and an additional fertilizer and supplied to plants, but the amount and yield of grown crops are generally limited even if the concentration of the nutrient elements in the fertilizer is increased, and by using the fertilizer in a larger amount, the nutrient elements come to be in excess in the soil thus worsening the balance of absorption and causing a reduction in plant growth, resulting in problems such as failure to achieve the intended increase in yield and failure to improve qualities such as sugar degree (Brix value) and freshness (greenness). Under these circumstances, combined use of various plant growth regulators has been carried out.

As the plant growth regulator, plant growth regulators represented by e.g. gibberellin and auxin are used in regulation of growth and morphogenetic reaction such as germination, rooting, elongation, flowering and fruit setting. Further, there are known techniques wherein a leaf spray using an oligosaccharide (JP-A 9-322647) or a liquid fertilizer containing sugars, minerals, amino acids, a seaweed extract or a microbial fermentation extract is sprayed onto leaves or applied in the form of a solution. JP-A 55-40674 discloses use of a C30 alcohol as a plant growth promoter. JP-A 2000-198703, equivalent to US-B 6 489 269, discloses a plant activating agent containing a C12 to C24 monovalent alcohol. JP-A 2002-265305, equivalent to US-A 2004-142822, discloses an agent for increasing the yield of crops, which contains a specific compound such as a C12 to 24 monovalent alcohol.

SUMMARY OF THE INVENTION

The present invention relates to a method of cultivating potato in an increased yield, which includes applying Compound (A) represented by the following general formula (1) at least once in a period from a planting stage to a flowering stage. The term "increased yield" means an increase in the amount of an intended site of harvested potato.

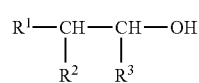

(1)

wherein $R^1$ represents a C10 to C22 hydrocarbon group, $R^2$ represents a hydrogen atom, a hydroxyl group or a C1 to C24 hydrocarbon group, and $R^3$ represents a hydrogen atom or a C1 to C24 hydrocarbon group.

DISCLOSURE OF THE INVENTION

In the prior art, there is a need for further improving an effect of increasing the final yield of crops. JP-A 2002-265305 supra refers to conditions regarded effective for increasing the yield of crops, but not to conditions that are optimum depending on the type of crops. In particular, the optimum conditions for potato such as white potato(*Solanum tuberosum* L.) and sweet potato(*Ipomoea batatas* Lam.) are not referred to.

The present invention provides a cultivating method more excellent in the effect of increasing the yield of crops, particularly potato.

According to the present invention, there is provided a method of cultivating potato in an increased yield wherein a significant effect of increasing the yield is stably achieved.

<Compound (A)>

In the general formula (1), the hydrocarbon groups represented by $R^1$, $R^2$ and $R^3$ may be respectively saturated or unsaturated groups, preferably saturated groups, and may be linear, branched or cyclic chains, preferably linear or branched chains, particularly preferably linear chains. The number of total carbons in the hydrocarbon group may be either an odd number or an even number, preferably an even number.

The number of total carbons in $R^1$, $R^2$ or $R^3$ is preferably 50 or less, more preferably 12 to 48, still more preferably 16 to 44.

In the general formula (1), the number of carbons in $R^1$ is preferably 14 to 22, more preferably 14 to 20, still more preferably 14 to 18. The number of total carbons in the compound represented by the general formula (1) is preferably 12 to 48, more preferably 16 to 28, still more preferably 16 to 24. The compound is more preferably a compound containing 12 to 24 carbons in total and having one hydroxyl group, still more preferably a compound containing 16 to 22 carbons in total and having one hydroxyl group. Examples of the compound represented by the general formula (1) include the followings:

(A1) 1-Alkanol represented by $CH_3(CH_2)_{o-1}OH$ wherein o is an integer of 12 to 24, preferably 16 to 24, more preferably 16 to 20, is mentioned. That is, the C12 to C24 monovalent alcohol is mentioned as the compound represented by the general formula (1). Specific examples include 1-dodecanol, 1-tridecanol, 1-tetradecanol, 1-pentadecanol, 1-hexadecanol, 1-heptadecanol, 1-octadecanol, 1-nonadecanol, 1-icosanol, 1-heneicosanol, 1-docosanol, 1-tricosanol, 1-tetracosanol etc.

(A2) 2-Alkanol represented by $CH_3CH(OH)(CH_2)_{p-3}CH_3$ wherein p is an integer of 12 to 24, preferably 16 to 24, more preferably 16 to 20, is mentioned. Specific examples include 2-dodecanol, 2-tridecanol, 2-tetradecanol, 2-pentadecanol, 2-hexadecanol, 2-heptadecanol, 2-octadecanol, 2-nonadecanol, 2-icosanol etc.

(A3) An alcohol unsaturated at the end thereof, represented by $CH_2=CH(CH_2)_{q-2}OH$ wherein q is an integer of 12 to 24, preferably 16 to 24, more preferably 16 to 20, is mentioned. Specific examples include 11-dodecen-1-ol, 12-tridecen-1-ol, 15-hexadecen-1-ol etc.

(A4) Other unsaturated long-chain alcohols include oleyl alcohol, elaidyl alcohol, linoleyl alcohol, linolenyl alcohol, eleostearyl alcohol (α or β), ricinoyl alcohol etc.

(A5) 1,2-Diol represented by $HOCH_2CH(OH)(CH_2)_{r-2}H$ wherein r is an integer of 12 to 24, preferably 16 to 24, more preferably 16 to 20, is mentioned. Specific examples include 1,2-dodecanediol, 1,2-tetradecanediol, 1,2-hexadecanediol, 1,2-octadecanediol etc.

Among the above-mentioned (A1) to (A5), (A1), (A2), (A4) and (A5) are preferable, (A1), (A2) and (A4) are more preferable, (A1) and (A4) are still more preferable, and (A1) is even more preferable.

In the present invention, the application of Compound (A) into potato can be carried out by a method of spraying a treating solution containing Compound (A) (referred to hereinafter as the treating solution) onto plant leaves or irrigating the treating solution in the soil or by a method of applying Compound (A) as granules directly to potato.

In the case of spraying onto plant leaves, the concentration of Compound (A) in the treating solution is preferably 1 to 1000 ppm, more preferably 20 to 600 ppm, still more preferably 60 to 200 ppm, and the amount of Compound (A) applied once by spraying is preferably 0.1 g/10 ares (hereinafter, "10 ares" is referred to as "10 a") to 100 g/10 a, more preferably 2 g/10 a to 60 g/10 a, still more preferably 6 g/10 a to 20 g/10 a. The concentration of Compound (A) in the treating solution is preferably regulated such that Compound (A) is applied in an amount in this range.

In the case of irrigating in the soil, the concentration of Compound (A) in the treating solution is preferably 1 to 1000 ppm, more preferably 10 to 500 ppm, still more preferably 30 to 200 ppm, and the amount of Compound (A) applied once by irrigating is preferably 3 g/10 a to 3000 g/10 a, more preferably 30 g/10 a to 1500 g/10 a, still more preferably 90 g/10 a to 600 g/10 a. The concentration of Compound (A) in the treating solution is preferably regulated such that Compound (A) is applied in an amount in this range.

In the case of application of Compound (A) in the form of granules, the amount of Compound (A) applied once is preferably 1 g/10 a to 10000 g/10 a, more preferably 10 g/10 a to 5000 g/10 a, still more preferably 50 g/10 a to 2500 g/10 a, further more preferably 100 g/10 a to 1200 g/10 a, even more preferably 300 g/10 a to 1000 g/10 a.

In the present invention, at least one member selected from a surfactant (B) [referred to hereinafter as component (B)] other than the compound (A), a chelating agent (C) [referred to hereinafter as component (C)] and a fertilizer (D) [referred to hereinafter as component (D)] is preferably applied together with the compound (A). Particularly, the components (B) and (C) are preferably simultaneously used. When the fertilizer is necessary at the time of application, for example the compounds (B), (C) and (D) are preferably used in combination with Compound (A). When the fertilizer is not necessary at the time of application, for example the components (B) and (C) are preferably used in combination with Compound (A).

<Component (B)>

As component (B), the following surfactant is used preferably for the purpose of emulsifying, dispersing or solubilizing Compound (A), or promoting the permeation of Compound (A).

The surfactant includes nonionic surfactants such as sorbitan fatty ester, polyoxyalkylene sorbitan fatty ester, polyoxyalkylene fatty ester, glycerin fatty ester, polyoxyalkylene glycerin fatty ester, polyglycerin fatty ester, polyoxyalkylene polyglycerin fatty ester, sorbitol fatty ester, polyoxyalkylene sorbitol fatty ester, sucrose fatty ester, resin acid ester, polyoxyalkylene resin acid ester, polyoxyalkylene alkyl ether, polyoxyalkylene alkyl phenyl ether, alkyl (poly)glycoside, polyoxyalkylene alkyl (poly)glycoside, alkyl alkanol amide, sugar-based fatty acid amide, etc. The sugar-based fatty acid amide includes, for example, those having a structure containing a hydrophobic group bound via an amide linkage to glucose or sugar alcohol, for example sugar-based fatty amides such as glucose or fructose fatty acid amides. Sugar or sugar alcohol having an amino group and containing a hydrophobic group bound via an amide linkage can be used, for example, sugar-based fatty acid amides such as N-methyl glucamine fatty acid amides. The nonionic surfactant is preferably at least one member selected from a nitrogen atom-free, ether group-containing nonionic surfactant and an ester group-containing nonionic surfactant. Preferable examples include polyoxyalkylene (particularly ethylene) sorbitan fatty ester, polyoxyalkylene (particularly ethylene) glycerin fatty ester, and sucrose fatty ester.

The surfactant includes anionic surfactants such as carboxylic acid-, sulfonic acid-, sulfate- and phosphate-based surfactants, and is preferably at least one member selected from carboxylic acid- and phosphate-based surfactants.

The carboxylic acid-based surfactant includes, for example, C6 to C30 fatty acid or salts thereof, polyvalent carboxylates, polyoxyalkylene alkyl ether carboxylates, polyoxyalkylene alkyl amide ether carboxylates, rosinates, dimer acid salts, polymer acid salts, tall oil acid fatty acid salts, esterified modified starch etc. Among these surfactants, esterified modified starch is preferable. Among this esterified modified starch, an alkenyl succinic acid-modified starch, alternatively called an alkenyl succinic acid-esterified starch or an alkenyl succinic acid starch, is preferable. Octenyl succinic acid starch is more preferable, for example Emulstar #30, produced by Matsutani Chem.Ind.Co.Ltd., as a commercial product.

The sulfonic acid-based surfactant includes, for example, alkyl benzene sulfonates, alkyl sulfonates, alkyl naphthalene sulfonates, naphthalene sulfonates, diphenyl ether sulfonates, alkyl naphthalene sulfonate condensates, naphthalene sulfonate condensates, etc.

The sulfate-based surfactant includes, for example, alkyl sulfates, polyoxyalkylene alkyl sulfates, polyoxyalkylene alkyl phenyl ether sulfates, tristyrene phenol sulfates, polyoxyalkylene distyrene phenol sulfates, alkyl polyglycoside sulfates etc.

The phosphate-based surfactant includes, for example, alkyl phosphates, alkyl phenyl phosphates, polyoxyalkylene alkyl phosphates, polyoxyalkylene alkyl phenyl phosphates etc.

The salt includes, for example, metal salts (Na, K, Ca, Mg, Zn etc.), ammonium salts, alkanol amine salts, fatty amine salts etc.

The amphoteric surfactants include amino acid-, betaine-, imidazoline- and amine oxide-based surfactants.

The amino acid-based surfactant includes, for example, acyl amino acid salts, acyl sarcosinate, acryloyl methyl amino propionate, alkyl amino propionate, acyl amide ethyl hydroxy ethyl methyl carboxylate, etc.

The betaine-based surfactant includes alkyl dimethyl betaine, alkyl hydroxy ethyl betaine, acylamide propyl hydroxy propyl ammonia sulfobetaine, ricinoleic acid amide propyl dimethyl carboxy methyl ammonia betaine, etc.

The imidazoline-based surfactant includes alkyl carboxy methyl hydroxy ethyl imidazolium betaine, alkyl ethoxy carboxy methyl imidazolium betaine, etc.

The amine oxide-based surfactant includes alkyl dimethyl amine oxide, alkyl diethanol amine oxide, alkyl amide propyl amine oxide etc.

The component (B) may be one kind of component or a mixture of two or more thereof. When the component (B) contains polyoxyalkylene groups, the component (B) is the one preferably having polyoxyethylene groups, wherein the number of these groups added on average is 1 to 300, preferably 5 to 100.

The component (B) is the one having a Griffin HLB of preferably 10 or more, more preferably 12 or more.

When a C12 to C24 monovalent alcohol is used as Compound (A), the component (B) is preferably at least one member selected from an ester group-containing nonionic surfactant, a nitrogen atom-free, ether group-containing nonionic surfactant, an amphoteric surfactant, a carboxylic acid-based anionic surfactant and a phosphate-based anionic surfactant. The component (B) is particularly preferably at least one member selected from an ester group-containing nonionic surfactant, a nitrogen atom-free, ether group-containing nonionic surfactant and esterified modified starch. Among these surfactants, esterified modified starch is especially preferable. Among this esterified modified starch, an alkenyl succinic acid-modified starch, alternatively called an alkenyl succinic acid-esterified starch or an alkenyl succinic acid starch, is preferable. Octenyl succinic acid starch is more preferable, for example Emulstar #30, produced by Matsutani Chem.Ind.Co.Ltd., as a commercial product. That is, the treating solution used in the present invention includes a solution containing a C12 to C24 monovalent alcohol and at least one kind of surfactant selected from an ester group-containing nonionic surfactant, a nitrogen atom-free, ether group-containing nonionic surfactant, an amphoteric surfactant, a carboxylic acid-based anionic surfactant and a phosphate-based anionic surfactant.

<Component (C)>

The following organic acid (or a salt thereof) having a chelating ability can be simultaneously used as the component (C) to further improve the effect of increasing the yield of crops. Specific examples include oxycarboxylic acids and polyvalent carboxylic acids such as citric acid, gluconic acid, malic acid, heptonoic acid, oxalic acid, malonic acid, lactic acid, tartaric acid, succinic acid, fumaric acid, maleic acid, adipic acid, glutaric acid etc., as well as salts thereof such as potassium salts, sodium salts, alkanolamine salts, fatty amine salts, etc. A chelating agent other than the organic acid can also be mixed to improve the yield of crops. The chelating agent mixed includes aminocarboxylic acid-based chelating agents such as EDTA, NTA, CDTA etc.

<Component (D)>

Specific examples of the component (D) include inorganic and organic materials serving as a source for supplying N, P, K, Ca, Mg, S, B, Fe, Mn, Cu, Zn, Mo, Cl, Si, Na etc., particularly N, P, K, Ca and Mg. Such inorganic materials include ammonium nitrate, potassium nitrate, ammonium sulfate, ammonium chloride, ammonium phosphate, soda nitrate, urea, ammonium carbonate, potassium phosphate, lime perphosphate, fused phosphate fertilizer ($3MgO \cdot CaO \cdot P_2O_5 \cdot 3CaSiO_2$), potassium sulfate, potassium chloride, lime nitrate, slaked lime, lime carbonate, magnesium sulfate, magnesium hydroxide, magnesium carbonate etc. The organic materials include fowl droppings, cow dung, bark manure, amino acid, peptone, Mieki (amino acid solution), fermentation extract, calcium salts of organic acids (citric acid, gluconic acid, succinic acid etc.), calcium salts of fatty acids (formic acid, acetic acid, propionic acid, caprylic acid, capric acid, caproic acid etc.), etc. These fertilizer components can also be used in combination with the surfactant. Incorporation of the fertilizer components is not always necessary where the fertilizer components have previously been applied sufficiently as a basal fertilizer to the soil. Incorporation of the fertilizer components is preferable for culture form such as a fertigation (a hydroponic soil culture) or hydroponics where the fertilizer components are given by irrigation while excessive application of the fertilizer is avoided.

When the components (B) to (C) are simultaneously used in the present invention, the ratio of each component to 100 parts by weight of Compound (A) is as follows: The component (B) is preferably 1 to 10,000 parts by weight, more preferably 10 to 1,000 parts by weight, still more preferably 50 to 500 parts by weight, further more preferably 100 to 300 parts by weight, and the component (C) is preferably 0 to 10,000 parts by weight, more preferably 0.1 to 1,000 parts by weight, still more preferably 5 to 200 parts by weight, further more preferably 10 to 100 parts by weight. In the case of a basal fertilizer, the amount of the component (D), in terms of nitrogen, is preferably 0.1 kg/10 a to 60 kg/10 a, more preferably 1 kg/10 a to 40 kg/10 a, still more preferably 5 kg/10 a to 20 kg/10 a, and in the case of an additional fertilizer applied once, the amount of the component (D), in terms of nitrogen, is preferably 1 g/10 a to 160 g/10 a, more preferably 2 g/10 a to 80 g/10 a, still more preferably 4 g/10 a to 40 g/10 a.

In the present invention, other nutrient sources (sugars, amino acids, vitamins etc.) can be used in an amount of 0 to 5000 parts by weight, particularly 10 to 500 parts by weight, based on 100 parts by weight of Compound (A).

The components (B) to (D) and other nutrient sources can be applied after being suitably incorporated into the treating solution, can be applied as such, or can be applied in a combined form thereof.

In the present invention, Compound (A) is applied at least once in a period from a planting stage to a flowering stage of potato.

When the treating solution is used, various means can be used as the method of supplying the treating solution to potato. Examples include a method of spraying the treating solution directly onto plant leaves, stems etc. or injecting it into the soil and a method of feeding the treating solution after diluting and mixing it with a hydroponic solution or supplied water contacting with roots in hydroponics or rock wool. The method of supplying the treating solution may be selected suitably depending on the type of potato and the time of application.

In cultivation of potato, there are usually a planting stage, a sprouting stage, a growing stage (particularly a stolon elongation stage), a flowering stage and a stage after the flowering stage until a harvest stage, and the preferable method of applying Compound (A) in each stage includes treatment with granules, spraying onto leaf surfaces, irrigating treatment, and hydroponic culture (hydroponics). In the planting stage, treatment with granules is preferable; in the sprouting stage and stolon elongation stage, treatment with granules, spraying onto leaf surfaces and irrigating treatment are preferable, and particularly, treatment with granules and spraying onto leaf surfaces are preferable. In the flowering stage, spraying onto leaf surfaces and irrigating treatment are preferable, and particularly spraying onto leaf surfaces is preferable. Compound (A) may be supplied at a predetermined concentration or a varying concentration within the above range in each stage.

The potato as the subject of the present invention includes white potato(*Solanum tuberosum* L.), sweet potato(*Ipomoea batatas* Lam.), a taro(*Colocasia antiaquorum*), a yam (*Dioscorea apposita* Thunb.) (specifically Nagaimo, Ichoimo, Tsukuneimo etc.), a Japanese yam(*Dioscorea japonica* Thunb.) (also called Yamaimo or Yamanoimo) and a Indian lotus (*Nelumbo nucifera* Gaertn.). In particular, white potato(*Solanum tuberosum* L.) is preferable. For classification of potatoes, "Yasai Engei Daihyakka 13 Jagaimo Satsumaimo Satoimo Nagaimo Renkon" (Vegetable Horticulture Encyclopedia 13, White Potato/Sweet Potato/Taro/Chinese Yam/Lotus Root)" (published on Jun. 15, 1999 by Rural Culture Association, Japan) can be referred to.

EXAMPLES

The present invention is described by reference to the following examples. The following examples are provided merely as illustrative of the invention and should not be construed to limit the present invention.

The treating solutions (balance: water) used in the Examples and Comparative Examples below are shown in Table 1.

TABLE 1

| Treating solution No. | Compound name | (A)/(B)/(C) ratio by weight |
|---|---|---|
| Product of the invention | | |
| 1 | (A): stearyl alcohol<br>(B): POE (20) sorbitane monooleate<br>(C): — | 25/75/0 |
| 2 | (A): stearyl alcohol<br>(B): POE (20) sorbitane monooleate<br>(C): EDTA•4Na | 23/69/8 |
| 3 | (A): 1,2-octadecane diol<br>(B): POE (20) sorbitane tristearate<br>(C): 3Na citrate | 23/69/8 |
| 4 | (A): 2-octadecanol<br>(B): POE (13) cetyl ether<br>(C): — | 33/67/0 |
| 5 | (A): stearyl alcohol<br>(B): octenyl succinic acid starch<br>(C): 3Na citrate | 41/41/8 |

TABLE 1-continued

| Treating solution No. | Compound name | (A)/(B)/(C) ratio by weight |
|---|---|---|
| Comparative product | | |
| 6 | (A): —<br>(B): POE (20) sorbitane monooleate<br>(C): — | 0/100/0 |
| 7 | (A): —<br>(B): POE (3) sodium lauryl sulfate<br>(C): — | 0/100/0 |
| 8 | (A): triacontanol<br>(B): POE (20) sorbitane monooleate<br>(C): — | 25/75/0 |

Example 1

White potato(*Solanum tuberosum* L.) (variety: Danshaku) was planted at 25-cm intervals in ridges at intervals of 80 cm. A basal dressing was applied such that the amounts of nitrogen, phosphate and potassium became 10 kg/10 a, respectively. Each of the treating solutions shown in Table 1 was used in treatment in a predetermined cultivation stage such that Compound (A) was applied at a concentration shown in Table 2. The treatment was spraying onto leaf surfaces in an amount of 100 L/10 a. The treating solution not containing Compound (A) was used such that the concentration of the component (B) became 360 ppm. The number of individual plants examined was 12 in each test section. In a suitable harvest stage, potato was harvested to examine the yield of the potato. In Table 2, the yield in each section is shown as a value relative to that (=100) of a non-treatment section.

TABLE 2 treatment stage in white potato cultivation
(○ indicates that the treatment was conducted.)

| Treating solution No. | Concentration of compond (A) (ppm) | Number of treatment times (total) | Planting stage→ | sprouting ←stage→ | Growing stage ←(leaf and stem→ elongation stage) stolon ←elongation→ stage | ←Flo-→ wering stage | Stage after ←flowering→ stage until harvest stage | ←harvest stage | yield |
|---|---|---|---|---|---|---|---|---|---|
| Example | | | | | | | | | |
| 1-1 | 5 | 120 | 3 | | ○ ○ ○ | | | | 145 |
| 1-2 | 5 | 120 | 3 | | | ○ ○ | ○ | | 129 |
| 1-3 | 5 | 120 | 1 | | ○ | | | | 136 |
| 1-4 | 5 | 120 | 5 | | ○ ○ | ○ ○ | ○ | | 142 |
| 1-5 | 5 | 600 | 3 | | ○ ○ ○ | | | | 132 |
| 1-6 | 5 | 1 | 3 | | ○ ○ ○ | | | | 120 |
| 1-7 | 5 | 120 | 3 | | | ○ ○ ○ | | | 130 |
| 1-8 | 1 | 120 | 3 | | ○ ○ ○ | | | | 145 |
| 1-9 | 2 | 120 | 3 | | ○ ○ ○ | | | | 144 |
| 1-10 | 3 | 120 | 3 | | | ○ ○ | ○ | | 128 |
| 1-11 | 4 | 120 | 3 | | | ○ ○ | ○ | | 127 |
| Comparative example | | | | | | | | | |
| 1-1 | 5 | 120 | 3 | | | | | ○ ○ ○ | 108 |
| 1-2 | 6 | — | 3 | | ○ ○ ○ | | | | 101 |
| 1-3 | 7 | — | 3 | | ○ ○ ○ | | | | 100 |
| 1-4 | 8 | 120 | 3 | | ○ ○ ○ | | | | 105 |
| Non-treatment | — | — | — | | | | — | | 100 |

Example 2

White potato(*Solanum tuberosum* L.) (variety: Dejima) was planted at 25-cm intervals in ridges at intervals of 80 cm. thereto over 60 seconds and mixed. The resulting mixture was tabletted into test granules having a regulated particle diameter of 2.0 mm. As the control, control granules not containing stearyl alcohol were prepared in the same manner.

TABLE 3

| | Treating solution | | | | Treatment stage in potato cultivation (○ indicates that the treatment was conducted.) | | | | | | |
|---|---|---|---|---|---|---|---|---|---|---|---|
| | | | | | | | Growing stage (leaf and stem elongation stage) | | Stage after ← flo-→ | | |
| Treatment method | No. | Concentration of compound (A) (ppm) | Amount of compound (A) applied (g/10a) | Number of treatment times (Total) | Planting stage→ | sprout- ←ing→ stage | Stolon ←elong-→ ation stage | Flower- ←ing→ stage | wering stage until harvest stage | Har- ←vest stage | Yield |
| Example | | | | | | | | | | | |
| 2-1  Soil irrigation | 5 | 120 | — | 3 | | | ○ | ○ | ○ | | 142 |
| 2-2  Soil irrigation | 5 | 120 | — | 3 | | | | ○○ | ○ | | 137 |
| 2-3  Soil irrigation | 5 | 120 | — | 1 | | ○ | | | | | 139 |
| 2-4  Granules | — | — | 720 | 1 | ○ | | | | | | 148 |
| 2-5  Granules | — | — | 720 | 1 | | | ○ | | | | 132 |
| Comparative example | | | | | | | | | | | |
| 2-1  Soil irrigation | 6 | — | — | 3 | | | ○ | ○ | ○ | | 101 |
| 2-2  Soil irrigation | 8 | 120 | — | 3 | | | ○ | ○ | ○ | | 99 |
| 2-3  Granules | — | — | — | 1 | ○ | | | | | | 100 |
| 2-4  Granules | — | — | — | 1 | | | ○ | | | | 101 |
| Non-treatment | — | — | — | — | | | | | | — | 100 |

A basal dressing was applied such that the amounts of nitrogen, phosphate and potassium became 10 kg/10 a, respectively. The treating solutions shown in Table 1, or test granules or control granules prepared by the method described later, were used in irrigating treatment of the soil or in treatment with the granules. The treating solutions shown in Table 1 were used such that Compound (A) was applied at a concentration shown in Table 3. The treating solution not containing Compound (A) was used such that the concentration of the component (B) became 360 ppm. Soil irrigation was conducted in an amount of 3000 L/10 a. The granules were used such that Compound (A) was applied in an amount shown in Table 3. The granules not containing Compound (A) were used such that the component (B) was applied in an amount of 2160 g/10 a. The number of individual plants examined was 12 in each test section. In a suitable harvest stage, potato was harvested to examine the yield of the potato. In Table 3, the yield in each section is shown as a value relative to that (=100) of a non-treatment section.

<Method of Preparing Test Granules>

A melt of 1.8 g stearyl alcohol and 5.4 g POE (20) sorbitan monooleate was dropped into and mixed with 4.8 g silicon dioxide, and 0.85 g 3Na citrate, 29.20 g talc, 1.68 g sodium bentonite, 39.83 g clay and 1.54 g lignin sulfonic acid were added thereto and mixed by a high-speed cutter. The mixing time and temperature were 60 to 90 seconds and 70° C., respectively. 15 g polyethylene glycol (weight-average molecular weight 6000) melted at 80° C. was added dropwise

The invention claimed is:

1. A method of cultivating potato in an increased yield, which comprises applying Compound (A) represented by the following general formula (1) at least once in a period from the end of a sprouting stage to the end of a stolon elongation stage,

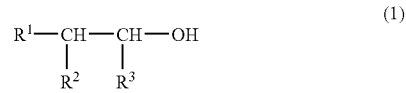
(1)

wherein $R^1$ represents a C10 to C22 hydrocarbon group, $R^2$ represents a hydrogen atom, a hydroxyl group or a C1 to C24 hydrocarbon group, and $R^3$ represents a hydrogen atom or a C1 to C24 hydrocarbon group.

2. The method of cultivating potato in an increased yield according to claim 1, wherein Compound (A) is a compound of the general formula (1) wherein $R^2$ and $R^3$ each represent a hydrogen atom.

3. The method of cultivating potato in an increased yield according to claim 1 or 2, which comprises applying at least one member selected from the group consisting of a surfactant (B) other than Compound (A), a chelating agent (C) and a fertilizer (D).

4. The method of cultivating potato in an increased yield according to claim 1, wherein the potato is white potato (*Solanum tuberosum* L.).

5. The method of cultivating potato in an increased yield according to claim 1, wherein said applying comprises spraying a solution comprising from 1 to 1,000 ppm of compound (A) onto leaves of white potato.

6. the method of cultivating potato in an increased yield according to claim 1, wherein $R^2$ represents a hydroxyl group.

* * * * *